United States Patent [19]

Taylor et al.

[11] 3,947,488

[45] Mar. 30, 1976

[54] O-ACYLATION USING ORGANOTHALLIUM COMPOUNDS

[76] Inventors: Edward C. Taylor; Alexander McKillop, both of 1500 Spring Garden St., Philadelphia, Pa. 19101

[22] Filed: May 21, 1974

[21] Appl. No.: 471,925

Related U.S. Application Data

[62] Division of Ser. No. 112,815, Feb. 4, 1971, Pat. No. 3,832,381, which is a division of Ser. No. 700,352, Jan. 25, 1968, Pat. No. 3,626,018.

[52] U.S. Cl............ 260/473 A; 260/410; 260/410.5; 260/410.9 R; 260/410.9 N; 260/484 A; 260/488 H; 260/488 R
[51] Int. Cl.²......................................... C07C 69/66
[58] Field of Search........ 260/484 A, 488 H, 473 A, 260/488 R, 410.5, 410.9 R, 410.9 N, 410

[56] References Cited

UNITED STATES PATENTS 2,336,317  12/1943  Thurston......................... 260/484 A

FOREIGN PATENTS OR APPLICATIONS 527,021  6/1956  Canada........................... 260/484 A

OTHER PUBLICATIONS

Chem. Abst., 52, 8108g, (1957).

J. Gen. Chem., (USSR), 27, 3084, (1957).

*Primary Examiner*—James A. Patten
*Assistant Examiner*—Paul J. Killos
*Attorney, Agent, or Firm*—Stuart R. Suter; Alan D. Lourie; William H. Edgerton

[57] ABSTRACT

Thallous salts of $\beta$-dicarbonyl compounds, prepared by reaction of the $\beta$-dicarbonyl compounds with a thallous alkoxide, are treated with alkyl halides to give C-alkyl products in high yield, with acyl halides at room temperature to give C-acyl products, and with acyl halides at low temperatures to give O-acyl products. Thallous phenolates are esterified with acyl or aroyl halides. Anhydrides are also prepared, as are biaryls and bi-sec-alkyls. N-Heterocyclics, including purines and pyrimidines, are N-alkylated. Lactams are O-acylated or N-alkylated.

7 Claims, No Drawings

O-ACYLATION USING ORGANOTHALLIUM COMPOUNDS

This is a divisional of Ser. No. 112,815 filed Feb. 4, 1971, U.S. Pat. No. 3,832,381 which is a divisional of Ser. No. 700,352, filed Jan. 25, 1968 now U.S. Pat. 3,626,018.

This invention relates to chemical processes. In particular, the invention relates to chemical processes utilizing organothallium compounds.

The present invention comprises processes for preparing organic compounds in high yield and in greater purity than previously possible, by treating organothallium compounds with alkyl, aroyl, and acyl halides, and Grignard reagents with thallous bromide. The invention comprises the preparation of a wide variety of compounds, including, but not limited to, C-alkylated and acylated β-dicarbonyl compounds, O-acylated β-dicarbonyl compounds, phenol ethers, phenol esters, anhydrides, 9-alkylated purines, biaryls, and hydrocarbons.

The first aspect of the invention comprises the C-alkylation of β-dicarbonyl compounds by treatment of a thallous salt of such a β-dicarbonyl compound, when such a salt is prepared by reation of the β-dicarbonyl compound with a thallous lower alkoxide, with an alkyl halide, preferably the iodide. Conventional alkylation of β-dicarbonyl compounds usually results in low yields of C-alkyl product, mixed with undesired products resulting from O-alkylation, cleavage, dialkylation, Claisen condensation, or coupling. The present method gives monoalkylated products in essentially quantitative yield under neutral conditions.

The thallous salts are readily prepared by the addition of a thallous lower alkoxide, preferably the ethoxide, to a solution of the β-dicarbonyl compound in an inert solvent such as benzene or petroleum ether. They may alternatively be prepared by direct exchange of thallium between the β-dicarbonyl compound and cyclopentadienyl thallium. The thallous salt of the β-dicarbonyl compound is then heated with an excess of an alkyl iodide, the thallous iodide being removed by filtration and the product isolated by simple distillation. Among the β-dicarbonyl compounds which may be used are β-keto esters such as ethyl acetoacetate, ethyl benzoylacetate, ethyl 2-benzoylpropionate, and ethyl 2-methyl-benzoylacetate; β-diketones such as acetylacetone, 3-acetyl-2,6-heptanedione, 1-benzoylacetone, triacetylmethane (3-acetyl-2,4-pentanedione), diacetylmethane (2,4-pentanedione), and dibenzoylmethane; and such cycloaliphatic compounds as 1,3-cyclopentanedione, 1,3-cyclohexanedione, 1,3-indanedione, and 2-carbethoxycyclopentanone. β-Diesters such as diethyl malonate may also be used. Alkylating agents having 1–10 carbon atoms, including methyl iodide, ethyl iodide, and isopropyl iodide may be used. Alkyl bromides may require higher reaction temperatures. The monoalkylated β-dicarbonyl compound may be converted to its thallous salt and then alkylated a second time.

A second aspect of the invention comprises the C-acylation of the thallous salts of β-dicarbonyl compounds with acyl fluorides, the thallous salts being prepared as described above. The thallous salt is suspended in ether and treated with the acyl fluoride. Thallous fluoride is then removed by filtration and the product distilled in high yield.

A third aspect of the invention comprises the O-acylation of β-dicarbonyl compounds by treating the thallous salt with an acyl halide at low temperatures approximating −78°. The O-acylated enol acylates are thereby obtained in high yield. Among the acyl halides which may be used for the acylations are such lower alkanoyl compounds as acetyl, propionyl, butyryl, pivaloyl, valeryl, and decanoyl halide.

A fourth aspect of the invention comprises the esterification of phenols by first forming the thallous phenolate by reaction of a phenol with a thallous alkoxide and then treating this salt with an acyl or aroyl halide. The reaction is conducted at room temperaure in a medium such as anhydrous ether. The thallous halide produced is filtered off and the solvent evaporated to give the phenol ester in yields approaching quantitative. The phenol employed may be substituted or unsubstituted, the possible substituents including, but not being limited to, lower alkyl, lower alkoxy, formyl, nitro, or halo. The phenol may also be an α or β-naphthol. Among the phenols which may be esterified are o-methoxyphenol, p-methoxyphenol, o-acetamidophenol, o-allylphenol, 4-benzyl-resorcinol, benzyl salicylate, 1-bromo-2-naphthol, p-butoxyphenol, p-tert-butylcatechol, 2-chloro-3,4-dimethylphenol, o-cresol, 4,6-dibromoresorcinol, 2,4-dichlorophenol, 2,6-dimethoxyphenol, ethyl salicylate, hydroquinone, 5-indanol, methyl salicylate, p-nitrophenol, pamoic acid, propyl gallate, salicylanilide, eugenol, thymol, and vanillin. The acyl halide may be a lower alkanoyl halide such as acetyl, propionyl, pivaloyl, or heptanoyl chloride. The aroyl halide may be benzoyl chloride or a substituted benzoyl chloride. In place of an acyl or aroyl halide, a sulfonyl halide may be used to give phenol sulfonates. Examples include toluenesulfonyl chloride and methanesulfonyl chloride.

A fifth aspect of the invention comprises the preparation of anhydrides by reaction of a thallous carboxylate with a stoichiometric amount of an acyl or aroyl halide. The reaction is conducted at room temperature in a medium such as ether. Removal of the thallous halide and evaporation of the solvent gives a virtually quantitative yield of ester. This method is useful for preparing both symmetrical and unsymmetrical (mixed) anhydrides. Conventional synthetic procedures for anhydride formation, even those utilizing other metal carboxylate salts, are not generally suitable for the preparation of mixed anhydrides because of the ease with which they may disproportionate above room temperature, either during their formation or in purification. In the present method, some disproportionation may be observed if the mixed anhydride formed is more reactive than the acid halide. It is therefore important to employ as a reactant the carboxylate salt of the weaker acid.

A further aspect of the use of thallous carboxylates for preparation of symmetrical anhydrides consists of the reaction of the thallous carboxylate with thionyl chloride in a solvent such as ether at room temperature. The intermediate acyl or aroyl sulfite spontaneously loses sulfur dioxide; evaporation of the ether gives the anhydride in very high yield after distillation. The carboxylate may be an aryl carboxylate, the aryl group being phenyl, tolyl, anisyl, halo-phenyl, or naphthyl; or an alkyl carboxylate, the alkyl group being methyl, ethyl, propyl, isopropyl, butyl, or tert-butyl. The aroyl or acyl halide may similarly be varied. Anhydrides with arylalkenyl carboxylic acids such as cinnamic may also be prepared. Among the anhydrides which may be prepared are n-butyric anhydride, maleic anhydride, chloromaleic anhydride, citraconic anhydride, glutaric anhydride, succinic anhydride, homophthalic anhydride, itaconic anhydride, propionic anhydride, triacetic anhydride, 1,2,4-benzenetricarboxylic anhydride, benzoic anhydride, mellitic trianhydride, naphthalic anhydride, phthalic anhydride, camphoric anhydride, propionic pivalic anhydride, and isobutyric pivalic anhydride.

A sixth aspect of the invention comprises the coupling of aryl and sec-alkyl magnesium bromides using thallous bromide to give biaryls and bi-sec-alkyls, respectively. Biaryls are customarily prepared from aryl halides, either by the classical Ullmann reaction or by coupling of aryl Grignard reagents with the halides of such metals as cobalt, copper, mercury, nickel, silver, or gold. The former method is laborious, inefficient, and expensive, both in terms of copper and glassware. The latter, with a few exceptions, is an extremely complex process which may lead to a multiplicity of products, and it is difficult to control. The present procedure involves refluxing the Grignard reagent and thallous bromide in a 1:2 molar ratio in a solvent or solvent-mixture such as benzene and/or tetrahydrofuran. The mixture is cooled, acidified, and filtered, and the product is obtained in high yield following purification on an alumina column and/or recrystallization. Biaryls which may be prepared include biphenyl, 4,4'-dimethoxy-biphenyl, 4,4'-dimethylbiphenyl, 3,3'-dimethylbiphenyl, 3,3',4,4'-tetramethylbiphenyl, 9,9'-bifluorene, N,N,N',N'-tetramethylbenzidine, 6,6'-dimethoxy-2,2'-binaphthyl, quaterphenyl, sexiphenyl, 4,4'-dichlorobiphenyl, 4,4'-difluorobiphenyl, and 2,2'-binaphthyl. Bi-sec-alkyls include bicyclohexyl, bicyclopentyl, 3,4-dimethyloctane, and other similar aliphatic compounds. o-Substituted aryl Grignard reagents do not give coupled products under the above conditions, and the present process does not comprise the preparation of o,o'-biaryls.

A seventh aspect of the invention comprises the N-alkylation of heterocyclic compounds having an NH or tautomerizable NH group. The process is expecially concerned with the alkylation of a substrate which does not also possess a hydrogen atom (or atoms) of equal or greater acidity relative to the NH group, e.g. another NH group, a hydroxy group, or a carboxy group. In that event, the process is operable, but larger quantities of reagent are required and the products are di- or polyalkylated.

A preferred group of heterocyclic compounds which can be alkylated advantageously are the purines. The manipulative disadvantages and synthetic limitations of the conventional techniques for alkylating purines are well-known. The present process provides a simple method for 9-alkylating purines by reaction of the thallous salt of the purine with an alkyl halide at room temperature in a solvent such as dimethylformamide. Purine substrates include purine itself, 6-chloropurine, adenine, and 6-substituted adenines. Alkyl halides include such simple alkyl compounds as methyl iodide and aralkyl halides such as benzyl bromide. The process also includes the reaction of a ribofuranoside with a purine to give a nucleoside. Among the nucleosides which may be prepared in this manner are adenosine, nebularine, adenine deoxyriboside, cordycepin, and puromycin. The latter compounds are antibiotics and all the nucleosides are of interest in view of the intense research efforts being devoted to cell metabolism and growth, cancer research, birth defects, and genetics. Among the heterocyclic compounds which may be alkylated by the present process are indoles and indolines including gramine, 5-benzyl-oxygramine, and isatins; pyrimidines including cytosine, thymine, thymidine, uracil, and uridine; and other heterocyclics such as carbazoles, pyrazoles, benzimidazoles, indazoles and imidazoles. The process also includes the N-alkylation of lactams. Among the lactams which may be N-alkylated are such compounds as pyridone and phenanthridone.

An eighth aspect of the invention comprises the O-acylation of lactams by treating the thallous salt of such a compound with an acyl halide. The products are 2-acyloxy heterocyclics. Among the products which may be prepared by this process in high yield are 2-acetoxypyridine and 2-benzoyloxy-pyridine. The acyloxy derivatives are best prepared by treatment of a chloroform suspension of the thallous salt with the appropriate acyl (or aroyl) halide. The reaction is mildly exothermic. After addition of the acid chloride, the mixture is stirred at room temperature for about 30 minutes to ensure complete reaction, and is then filtered to remove thallous chloride. Removal of the solvent then gives the desired product. Other solvents such as ether or benzene have proven useful in place of chloroform; meticulous drying of these solvents prior to use is not necessary. For halides which are not particularly reactive (such as tosyl chloride or mesitoyl chloride), the mixture may be refluxed for a few hours.

The processes of the invention are useful for preparing a wide variety of compounds in higher yield or having a greater degree of purity than hitherto possible. They are also useful for preparing compounds hitherto inaccessible or difficulty accessible. The compounds prepared by these processes are useful in chemical research as intermediates for preparing a wide variety of compounds of potential use in the chemical, pharmaceutical, petroleum, plastics, and other related industries. They also have definite uses themselves in these fields.

The C-alkylated and acylated β-dicarbonyl compounds, having reactive carbonyl groups, are highly useful to chemists and can be condensed with amines and other compounds bearing reactive hydrogen atoms. They are useful for forming 4-alkylpyrazoles, 5-alkylpyrimidines, 2,3-dialkyl-1,4-dicarbonyl compounds (by coupling), in chain extension, i.e., synthesis of ketones by ester cleavage of C-alkylated β-keto esters; in the synthesis of long-chain esters by ketone cleavage; and in the synthesis of coumarins and flavones.

The O-acylated β-dicarbonyl compounds are useful as acylating agents, in the synthesis of β-aminocrotonates, as protection for dicarbonyl compounds, regenerated by hydrolysis; and for converting an acid chloride into a neutral acylating agent.

The phenol esters are useful for the preparation of pharmaceuticals (such as aspirin), and as derivatives of phenols for identification and isolation (such as a 2,4-dinitrobenzoyl derivative, useful as a solid derivative for isolation); as protection for phenols during oxidation and substitution reactions; as intermediates for the synthesis of aryl ketones by the Fries rearrangement (of phenol esters); and as intermediates for the synthesis of aryl ketones (by reaction with Grignard reagents and aryl lithium reagents).

The anhydrides are useful for the synthesis of acylated or aroylated derivatives of amines, amino acids (as protecting groups), phenols, thiophenols, mercaptans, alcohols, active methylene compounds, aromatic hydrocarbons, enamines, hydrazines; as reagents for the conversion of oximes to nitriles by dehydration; as reagents for the conversion of 5-nitroso-6-aminopyrimidines to 2-cyano-1,3,5-triazines; and as intermediates for ketone synthesis by reaction with Grignard reagents.

The alkylated heterocyclics are useful as derivatives for purposes of isolation; as antibiotics, in the case of puromycin, cordycepin, and nebularine; as intermediates for preparing important, physiologically essential nucleotides and nucleosides; and for preparing useful pharmaceutical agents such as 6-mercaptopurine riboside.

The biaryls are useful as intermediates for the synthesis of a large variety of condensed systems, such as carbazoles, dibenzofurans, phenanthridines, benzcoumarins, and fluorenes.

The bi-sec-alkyls are useful, inter alia, as standards in the petroleum industry, for example, 3,4-dimethyloctane.

As indicated above, the known compounds prepared by the processes of the present invention are themselves known to be useful for a variety of purposes. Among these uses may be recited the following:

β-Dicarbonyl compounds are known as polymerization initiators, oxidation initiators, stabilizers, and substrates for preparing chelating agents. For example, β-diketones such as 3-methylpentane-2,4-dione and β-keto esters such as ethyl 2-methylacetoacetate and ethyl 2-ethylacetoacetate are known to be polymerization initiators in the polymerization of such monomers as methyl methacrylate, acrylonitrile, styrene, and vinyl acetate. β-Diketones such as pentane-2,4-dione, 3-ethylpentane-1,3-dione, 1,3-cyclopentanedione, 2-acetyl-cyclohexanone, 4-methylheptane-3,5-dione, triacetylmethane, and dibenzoylmethane are known as oxidation initiators in the production of hydroperoxides. Malonic esters such as diethyl malonate, methyl ethyl malonate, diethyl isobutylmalonate, and dicyclohexyl malonate are also known as oxidation initiators for the production of hydroperoxides. Tribenzoylmethane, dipropionylmethane, and benzoylacetone are known as substrates for preparing chelates with rare earth elements. Ethyl 2-acetylacetoacetate and other β-diketones are known to be substrates for preparing chelates with copper, used as stabilizers for liquid polyphenyl ethers. Acetyldibenzoylmethane is known to be an intermediate for preparing medicinals.

Biaryls are known to have various uses. 4,4-Dichlorobiphenyl is known as a solvent in the manufacture of toluene diisocyanate. Biphenyl is known as a fungicide for oranges and other citrus fruit. N,N,N',N'-Tetramethylbenzidine is known as a redox indicator. p-Quaterphenyl is known to be a nuclear reaction moderator and an agent for staining polymeric film. Compounds such as 4,4'-dimethoxybiphenyl and 2,2'-binaphthyl are known to be liquid scintillator solutes. Compounds such as 4,4'-dimethylbiphenyl and 3,3',4,4'-tetramethylbiphenyl are known to be starting materials for polymers. Biaryl compounds in general are known to be suitable as starting materials in the production of polymeric products for use in the paint industry and for the production of synthetic fibers in the textile industry. Bi-sec-alkyls such as bicyclohexyl are known to be components of penetrating oils.

Phenyl acetate is known as a diesel fuel additive. Phenyl benzoate is known as a chain transfer agent in formaldehyde polymerization. p-Nitrophenyl pivalate is known as an acetylating agent. Naphthyl acetates and butyrates are known to be used as fluorogenic substrates in the assay of anticholinesterases. Such esters as naphthyl and phenyl benzoates are used as dye carriers.

Anhydrides in general, including isobutyric anhydride and acetic benzoic anhydride, are known to be used as cyclizing agents for preparing polyimides. Benzoic anhydride is known to be a chain-transfer agent for formaldehyde polymerization.

The following examples are intended to illustrate the processes of the invention, but are not to be construed as limiting the scope thereof. Temperatures stated are in degrees Centigrade.

EXAMPLE 1

3-Methylpentane-2,4-dione (diacetylethane)

Acetylacetone (0.11 mole) is stirred in 50l ml. of petroleum ether and 0.10 mole of thallous ethoxide, added all at once. The mixture is stirred for 2–3 minutes, chilled, and filtered to give a quantitative yield of acetylacetonatothallium.

A suspension of 10.10 g. (0.033 mole) of this thallous salt of acetylacetone in 100 ml. of freshly distilled methyl iodide is heated under reflux with stirring for 5 hours. The mixture is then cooled, filtered through Celite (to remove thallous iodide), the excess methyl iodide recovered by flash evaporation, and the residue distilled to give 3.7 g. (100%) of 3-methylpentane-2,4-dione, b.p. 78°–80°mm.

EXAMPLE 2

1,1,1-Triacetylethane

A suspension of 5.0 g. (0.014 mole) of the thallous salt of triacetylmethane, prepared as in Example 1, in 30 ml. of freshly distilled methyl iodide is heated under reflux for 6 hours, cooled to room temperature, and filtered through Celite. The filtrate is distilled (flash evaporation) to remove (recover) excess methyl iodide, and the crude product distilled to give 2.8 g. (100%), b.p. 87°/20 mm. of 1,1,1-triacetylethane. The pure product solidifies upon standing to give white, tacky crystals, m.p. 33°–35°.

Anal: Calcd. for $C_8H_{12}O_3$: C, 61.52; H, 7.75. Found: C, 61.42; H, 7.72.

EXAMPLE 3

When the thallous salts of ethyl acetoacetate, 2-carbethoxycyclopentanone, ethyl benzoylacetate, and ethyl 2-methylbenzoylacetate, prepared according to Example 1, are refluxed with methyl iodide as described in Example 1 for periods of about 4, 9, 4, and 14 hours, respectively, ethyl 2-methylacetoacetate (b.p. 82°/25 mm.), 2-methyl-2-carbethoxy-cyclopentanone (b.p. 124°–126°/35 mm.), ethyl 2-methylbenzoyl acetate (b.p. 96°–97°/0.25 mm.), and ethyl 2,2-dimethylbenzoyl-acetate (b.p. 98°–100°/0.35 mm.), respectively, are obtained in quantitative yield.

When the thallous salts of ethyl acetoacetate, acetylacetone, 2-carbethoxycyclopentanone, ethyl benzoylacetate, and ethyl 2-methylbenzoylacetate, prepared according to Example 1, are refluxed with ethyl iodide as described in Example 1 for periods of about 4, 16, 9, 4, and 14 hours, respectively, ethyl 2-ethylacetoacetate (b.p. 94°–96°/25 mm.), 3-ethylpentane-2,4-dione (78°–80°/17 mm.), 2-ethyl-2 -carbethoxy-cyclopentanone (b.p. 134°–136°/37 mm.), ethyl 2-ethylbenzoylacetate (b.p. 150°–152°/0.6 mm.), and ethyl 2-ethyl-2 -methyl-benzoylacetate (b.p. 100°–102°/0.3 mm.), respectively, are obtained in greater than 90% yield.

When the thallous salts of ethyl acetoacetate, acetylacetone, 2 -carbethoxycyclopentanone, ethyl benzoylacetate, and ethyl 2-methylbenzoylacetate, prepared according to Example 1, are refluxed with isopropyl iodide as described in Example 1 for periods of about 15, 14, 12, 22, and 14 hours respectively, ethyl 2isopropylacetoacetate (b.p. 90°–92°/18 mm.), 3-isopropylpentane-2,4-dione (b.p. 94°/45 mm.), 2-isopropyl-2-carbethoxycyclopentanone (b.p. 136°–138°/37 mm.), ethyl 2-isopropylbenzoylacetate (b.p. 108°–110°/0.5 mm.), and ethyl 2-isopropyl-2-methyl-benzoylacetate (b.p. 116°–118°/0.35 mm.), respeectively, are obtained in at least 90% yield.

EXAMPLE 4

Triacetylmethane

Gaseous acetyl fluoride is bubbled into a suspension of 30.0 g. (0.1 mole) of the thallous salt of acetylacetone in 150 ml. of dry tetrahydrofuran, under nitrogen, at a rate of 3.0 cc./minute for a total of 30 minutes. After filtration through Celite, the solution is concentrated and the residue distilled to give 13.5 g. (96%), b.p. 90°–95°/1.0 mm.

Anal: Calcd. for $C_7H_{10}O_3$: C, 59.14 H, 7.09. Found: C, 59.34, H, 7.27.

EXAMPLE 5

When the thallous salts of ethyl acetoacetate, 2-carbethoxycyclopentanone, and 3-methylpentane-2,4-dione, prepared according to Example 1, are treated with acetyl fluoride at room temperature as described in Example 4, ethyl 2-acetyl-acetoacetate, 2-acetyl-2-carbethoxycyclopentanone, and 3-acetyl-3-methylpentane-2,4-dione, respectively, are obtained in 95% yield. Tribenzoylmethane is prepared by treating the thallous salt of dibenzoylmethane with benzoyl fluoride in the same manner. Acetyldibenzoylmethane is prepared by treating the thallous salt of dibenzoylmethane with acetyl fluoride.

EXAMPLE 6

When the thallous salts of ethyl acetoacetate, acetylacetone, 2-carbethoxycyclopentanone, and ethyl benzoylacetate, prepared according to Example 1, are treated with acetyl chloride in ether −78°, the corresponding enol acetates are obtained in 90% yield.

EXAMPLE 7

4,4'-Dichlorobiphenyl

Thallous bromide (22.46 gm, 0.079 mole) is added to a solution of p-chlorophenyl magnesium bromide (0.0395 mole) in a mixture of benzene (25 ml.) and tetrahydrofuran (25 ml.) and the mixture stirred and refluxed under nitrogen for 7 hours. The reaction mixture is cooled, poured into 150 ml. of dilute hydrochloric acid, and the 4,4'-dichlorobiphenyl extracted with ether (2 × 30 ml.). The combined extracts are dried over anhydrous sodium sulfate, and the solvent removed to leave 2.9 gm. of crude white product. This is filtered through a short column of alumina using chloroform as eluent, to give, after removal of the solvent, 2.70 gm. (61%) of pure 4,4'-dichlorobiphenyl, m.p. 148°.

EXAMPLE 8 p-Quaterphenyl

A mixture of thallous bromide (2 moles) and p-biphenyl magnesium bromide (1 mole) is stirred and refluxed under nitrogen in benzene-tetrahydrofuran (1:1) for 5 hours. The mixture is then chilled to 0° and the mixture of p-quaterphenyl and metallic thallium filtered off. Extraction of these solids with boiling nitrobenzene (30 ml.) gives a 70% yield of pure p-quaterphenyl as colorless plates, m.p. 320°.

EXAMPLE 9

N,N,N',N'-Tetramethylbenzidine

A mixture of p-dimethylaminophenyl magnesium bromide (1 mole) and thallous bromide (2 moles) is stirred and refluxed under nitrogen for 5 hours. The cooled solution is filtered to remove thallium, and hydrogen chloride passed into the filtrate. The colorless hydrochloride which precipitates is filtered off, stirred into dilute sodium hydroxide, and the tetramethylbenzidine extracted with ether-benzene (1:1, 2 × 30 ml.) The extracts are dried over anhydrous sodium sulfate and the solvent removed to leave a yellow solid which is sublimed at 165°/0.05 mm. to give a 70% yield of pure N,N,N',N'-tetramethylbenzidine as a colorless solid, m.p. 195°.

EXAMPLE 10

When bromobenzene, p-bromoanisole, p,-bromotoluene, m-bromotoluene, 4-bromo-o-xylene, 2-bromo-6-methoxynaphthalene, 4-fluorobromobenzene, 2-bromonaphthalene, cyclohexyl bromide, cyclopentyl bromide, and 2-bromopentane are converted to Grignard reagents and treated with thallous bromide according to the procedure of Example 7, biphenyl 4,4'-dimethoxybiphenyl, 4,4'-dimethylbiphenyl, 3,3'-dimethylbiphenyl, 3,3',4,4'-tetramethylbiphenyl, 6,6'-dimethoxy-2,2'binaphthyl, 4,4'-difluorobiphenyl, 2,2'-binaphthyl, bicyclohexyl, bicyclopentyl, and 3,4-dimethyloctance, respectively, are obtained in up to 90% yield.

EXAMPLE 11

The general procedure for the conversion of phenols to phenol esters through the intermediate formation of thallous salts is illustrated by the formation of phenyl acetate.

To a stirred solution of phenol (6.58 g., 0.07 m) in benzene (150 ml.), previously heated to just below reflux temperature, is added in one lot, a solution of thallous ethoxide (17.43 g., 0.07 m.) in anhydrous benzene (50 ml.). Within a few minutes thallous phenoxide precipitates, is filtered off and dried under vacuum to give 23.05 g., 98%, m.p. 231°–235°.

A vigorously stirred suspension of thallous phenoxide (5 g., 0.017 m.) in anhydrous ether (15 ml.) is treated dropwise with freshly distilled acetyl chloride (1.33 g., 0.017 m.) in anhydrous ether (3 ml.) over 5 mins. at such a rate that the exothermic reaction is controlled. The mixture is then stirred for 1 hour at room temperature, the precipitated thallous chloride removed by filtration through Celite and the solvent evaporated under vacuum. The residual colorless oil is distilled to give phenyl acetate, 2.27 g., 98%, b.p. 110°/58 mm.

Phenol esters prepared by the above process are phenyl pivalate, b.p. 112°/25 mm.; phenyl benzoate, m.p. 70°; p-nitrophenyl acetate, m.p. 79°–80°; p-nitrophenyl pivalate, m.p. 95°–97°; p-nitrophenyl benzoate, m.p. 144°–145°; o-methoxyphenyl acetate, m.p. 35°–36°; o-methoxyphenyl pivalate, b.p. 140°/1.7 mm.; o-methoxyphenyl benzoate, b.p. 205°/15 mm.; p-methoxyphenyl acetate, m.p. 35–36°; p-methoxyphenyl pivalate, b.p. 142°/18mm.; p-methoxyphenyl benzoate, m.p. 88°–89°; β-naphthyl acetate, m.p. 70°–71°; β-naphthyl pivalate, m.p. 65.5°–66°; and β-naphthyl benzoate, m.p. 106.5°–107°.

EXAMPLE 12

The general procedure for the preparation of mixed and symmetrical anhydrides using acid chlorides is illustrated by the formation of benzoic pivalic anhydride.

A solution of thallous ethoxide (17.43 g., 0.07 m.) in ether (200 ml.) is rapidly added to a stirred solution of benzoic acid (8.54 g., 0.07 m.) in warm ether (500 ml.). The precipitated salt is filtered, recrystallized if necessary (aqueous ethanol), and dried under vacuum. Yield, 95°–99%, m.p. 340°.

A solution of freshly distilled pivalyl chloride (1.205 g., 0.01 m.) in anhydrous ether (3 ml.) is added to a stirred suspension of finely ground thallous benzoate (3.25 g., 0.01 m.) in anhydrous ether (20 ml.) and the mixture stirred at 25°until the acyl halide has completely reacted, as shown by the absence of the C-Cl stretching frequency in the I.R. spectra of aliquots removed at regular intervals (reaction time approximately 8 hrs). The precipitated thallous chloride is then removed by filtration through Celite and the solvent evaporated under reduced pressure at less than 30° to give 2.06 g. (99%) of the product.

Other compounds prepared by this procedure are acetic benzoic anhydride (0.25 hours at 5°); benzoic isobutyric anhydride (6 hours at 25°); benzoic pivalic anhydride (8 hrs. at 25°); benzoic anhydride (4 hrs. at 35°, m.p. 42°); acetic pivalic anhydride (0.25 hrs. at 5°); isobutyric pivalic anhydride (1 hr. at 25°); pivalic anhydride (1 hr. at 25°, b.p. 190°); acetic isobutyric anhydride (0.25 hrs. at 5°); isobutyric anhydride (1 hr. at 25°, b.p. 182°); and acetic formic anhydride (3 hrs. at 5°, gradually warmed to 25°, b.p. 35°/18 mm.). Propionic pivalic anhydride is similarly prepared.

EXAMPLE 13

The procedure for preparing symmetrical anhydrides using thionyl chloride is illustrated by the formation of benzoic anhydride.

A solution of freshly purified thionyl chloride (0.595 g., 0.005 m.) in anhydrous ether (3 ml.) is added dropwide to a stirred suspension of powdered thallous benzoate (3.25 g., 0.01 m.) in anhydrous ether (15 ml.). After stirring at room temperature for 1 hr., nitrogen is bubbled through the reaction mixture for 15 mins. to remove sulfur dioxide. The precipitated thallous chloride is then filtered off and the solvent removed under reduced pressure to yield an oil which rapidly solidifies. Recrystallization from benzene-pentane mixture gives a 97% yield; m.p. 42°.

Other products prepared by this procedure are pivalic anhydride, b.p. 190°; isobutyric anhydride, b.p. 182°; and acetic anhydride, b.p. 140°.

EXAMPLE 14

2-Acetoxypyridine

To a solution of 13.30 g. (0.14 mole) of 2-pyridone in 300 ml. of a mixture of pentane and ethanol (very little ethanol, just enough to effect solution) was added 10 ml. (0.14 mole) of thallous ethoxide. The thallous salt was removed by filtration to give 40.77 g. (98%), m.p. 152°–155°. If desired, it may be recrystallized from ethanol.

Anal. Calcd. for $C_5H_4NOTl$: C, 20.12; H, 1.35; N, 4.69. Found: C, 19.92; H, 1.37; N, 4.65.

To a suspension of 9.86 g. (0.330 mole) of the thallous salt of 2-pyridone in 50 ml. of dry ether was added 2.75 g. (0.328 mole + 10% excess) of freshly distilled acetyl chloride over a period of about 10 minutes. After addition was complete, the reaction mixture was stirred for 30 minutes, the white solid which separated filtered off and the ether filtrate evaporated to give 4.40 g. (98%) of pure (vpc) 2-acetoxypyridine.

EXAMPLE 15

2-Benzoyloxypyridine

To a suspension of 10.0 g. (0.033 mole) of the thallous salt of 2-pyridone in 50 ml. ether was added 4.5 g. (0.032 mole) of freshly distilled benzoyl chloride over a period of 10 minutes. The mixture was stirred at room temperature for 15 minutes, thallous chloride separated by filtration and the ether filtrate evaporated to give 5.81 g. (90%) of pure 2-benzoyloxypyridine, m.p. 39°–41°.

Anal. Calcd. for $C_{12}H_9NO_2$: C, 72.35; H, 4.55; N, 7.03. Found: C, 72.16; H, 4.61; N, 7.18.

Other products prepared by this procedure are 2-(3,5-dinitrobenzoyloxy)pyridine (88%), 2-mesitoyloxypyridine (86%), 2-pivaloyloxypyridine (93%), and 2-p-anisoyloxypyridine (100%).

EXAMPLE 16

5-Methyl-6(5H)-phenanthridone

To a suspension of 1.15 g. (5.88 mmole) of phenanthridone in 35 ml. of dimethylformamide (under nitrogen) was added 1.46 g. (5.88 mmole) of thallous ethoxide. As soon as the solution became homogeneous (30 second), 1.034 g. (5.88 mmole) of methyl iodide was added all at once. Thallous iodide began to separate immediately. After 30 minutes; the mixture was filtered, the dimethylformamide filtrate evaporated under reduced pressure to about 15 ml., and water added. Filtration give 1.15 g. (95%) of 5-methyl-6(5H)-phenanthridone, m.p. 108°.

By the use of ethyl iodide rather than methyl iodide, 5-ethyl-6 (5H)phenanthridone was prepared in 97% yield (m.p. 87°–90°).

EXAMPLE 17

9-Benzyladenine

To a solution of 1.0 g. of adenine in dimethylacetamide was added dropwise a solution of thallous ethoxide dissolved in ethanol. Addition was stopped when no further precipitation of the thallous salt of adenine could be observed. After 5 hrs., the thallous salt was collected by filtration. (A small quantity of additional thallous salt could be obtained by concentration of the filtrate and further addition of thallous ethoxide). The combined thallous salts weighed 2.3 g. (94%), m.p.

330°.

Anal. Calcd. for $C_5H_4N_5Tl$: C, 17.75; H, 1.18; N, 20.71. Found: C, 18.01; H, 1.35; H, 20.42.

To a suspension of 2.3 g. of the thallous salt of adenine in 30 ml. of dimethylformamide was added 1.1 g. of benzyl bromide, with vigorous stirring. After 10 hours at room temperature, thallous bromide was removed by filtration and the filtrate concentrated to dryness under reduced pressure. The solid residue was crystallized from ethanol to give 0.77 g. (45%) of 9-benzyladenine, m.p. 230°, identical with an authentic sample.

EXAMPLE 18

6-Chloro-9-benzylpurine

To a clear solution of 1.0 g. of 6-chloropurine in 20 ml. of absolute ethanol at room temperature was added dropwise a solution of thallous ethoxide in ethanol until no further precipitation of the thallous salt of 6-chloropurine was observed. After 5 hours, the mixture was filtered to give 2.0 g. (87%), m.p. 330°.

Anal. Calcd. for $C_5H_2N_4ClTl$: C, 16.76; H, 0.56; N, 15.66. Found: C, 16.79; H, 0.62; N, 15.64.

To a suspension of 2.0 g. of this thallous salt in 20 ml. of dimethylformamide was added 0.8 g. of benzyl bromide dropwise, at room temperature, with vigorous stirring. After 5 hours, the mixture was filtered to remove thallous bromide and the filtrate concentrated to dryness under reduced pressure. The residue was washed with water, and the residual solid dried and then repeatedly extracted with ether-petroleum ether. Concentration of the extracts gave 0.95 g. (60%), m.p. 78°, of 6-chloro-9-benzylpurine, identical with an authentic sample.

EXAMPLE 19

9-Benzylpurine

To a room temperature of 0.5 g. of purine in 15 ml. of ethanol was added an ethanol solution of thallous ethoxide until no further precipitation of the thallous salt of purine was observed. The reaction mixture was allowed to stand at room temperature for several hours and was then filtered. The filtrate was concentrated and more thallous ethoxide in ethanol added to give an additional amount of the thallous salt of purine; combined yield 1.2 g. (90%), m.p. 255°dec.

Anal. Calcd. for $C_5H_3N_4Tl$: C, 18.58; H, 0.93; N, 17.03. Found: C, 18.46; H, 0.93; N, 16.98.

To a suspension of 1.2 g. of the above thallous salt in 20 ml. of dimethylformamide was added 0.64 g. of benzyl bromide with vigorous stirring. As the reaction proceeded, the color of the solution changed to a light yellow. After 5 hours of stirring at room temperature, the suspended thallous bromide was removed by filtration and the filtrate concentrated to dryness under reduced pressure. The residue was dissolved in chloroform and passed through a silica-gel column. Evaporation of the eluate gave a crystalline solid which was extracted with a large volume of 1:1 ether-petroleum ether. Concentration of the extracts followed by cooling gave 0.45 g. (50%, based upon purine) of colorless needles, m.p. 95°. One recrystallization from ether-petroleum ether (1:1) raised the melting point to 99°–100°. The product was identical with an authentic sample of 9-benzylpurine.

Nebularine was prepared by the use of the thallous salt of purine in the procedure of Brown et al., J. Biol. Chem. 204, 1019 (1953), in place of the chloromercuri salt used therein. The thallous salt of purine is condensed with chlorotriacetylribofuranose and the resulting acetyl derivative hydrolyzed to the product with methanol-ammonia. Other experimental conditions were identical. Crystalline nebularine was obtained after chromatography of the crude product on silica-gel with chloroform.

We claim:

1. A process for O-acylating a β-dicarbonyl compound, said β-dicarbonyl compound having a methylene group between the carbonyl groups, comprising treating the thallous salt of such a β-dicarbonyl compound, prepared by reaction of the β-dicarbonyl compound with a thallous lower with a lower alkanoyl halide of up to 10 carbon atoms at a temperature of about −78°.

2. A process for O-acylating a β-dicarbonyl compound according to claim 1 comprising treating the thallous salt of ethyl acetoacetate acetylacetone, 2-carbethoxycyclopentanone, or ethyl benzoylacetate with a lower alkanoyl halide of up to 10 carbon atoms at a temperature of about −78°.

3. A process for O-acylating a β-dicarbonyl compound according to claim 2 in which the acyl halide is acetyl, propionyl, butyryl, pivaloyl, valeryl, or decanoyl halide.

4. A process for O-acylating a β-dicarbonyl compound according to claim 3 comprising treating the thallous salt of ethyl acetoacetate with acetyl chloride at about −78°.

5. A process for O-acylating a β-dicarbonyl compound according to claim 3 comprising treating the thallous salt of acetylacetone with acetyl chloride at about −78°.

6. A process for O-acylating a β-dicarbonyl compound according to claim 3 comprising treating the thallous salt of 2-carbethoxycyclopentanone with acetyl chloride at about −78°.

7. A process for O-acylating a β-dicarbonyl compound according to claim 3 comprising treating the thallous salt of ethyl benzoylacetate with acetyl chloride at −78°.

* * * * *

UNITED STATES PATENT AND TRADEMARK OFFICE
CERTIFICATE OF CORRECTION

PATENT NO. : 3,947,488
DATED : March 30, 1976
INVENTOR(S) : Edward C. Taylor and Alexander McKillop It is certified that error appears in the above—identified patent and that said Letters Patent are hereby corrected as shown below:

Claim 1 should read as follows:

"1. A process for O-acylating a β-dicarbonyl compound, said β-dicarbonyl compound having a methylene group between the carbonyl groups, comprising treating the thallous salt of such a β-dicarbonyl compound with a lower alkanoyl halide of up to 10 carbon atoms at a temperature of about $-78°$."

Signed and Sealed this

Twentieth Day of July 1976

[SEAL]

Attest:

RUTH C. MASON
Attesting Officer

C. MARSHALL DANN
Commissioner of Patents and Trademarks